| United States Patent [19] | [11] Patent Number: 4,590,202 |
| Remy | [45] Date of Patent: May 20, 1986 |

[54] N-(2-IMIDAZOLIDINYLIDENE)-5H-DIBENZO[A,D]CYCLOHEPTEN-5-AMINE COMPOUNDS AND $\alpha_2$-ADRENERGIC ANTAGONISTIC USES THEREOF

[75] Inventor: David C. Remy, North Wales, Pa.

[73] Assignee: Merck & Co., Inc., Rahway, N.J.

[21] Appl. No.: 571,981

[22] Filed: Jan. 19, 1984

[51] Int. Cl.⁴ .................. C07D 403/30; A61K 31/415
[52] U.S. Cl. ..................................... 514/392; 548/315
[58] Field of Search .................. 548/315; 424/273 R; 514/392

[56] References Cited

U.S. PATENT DOCUMENTS 2,985,660  5/1961  Judd et al. ............................ 548/315
3,014,911  12/1961  Engelhardt ......................... 548/315

OTHER PUBLICATIONS

J. Med. Chem. 8, pp. 829–835 (1965) Engelhardt et al.
Merck Index vol. 10, pp. 398–399 (1983).
Lowe, et al., Br. J. Pharmac., 74, pp. 651–663, (1981).

*Primary Examiner*—Henry R. Jiles
*Assistant Examiner*—Robert C. Whittenbaugh
*Attorney, Agent, or Firm*—Alice O. Robertson; Michael C. Sudol

[57] ABSTRACT

N-(2-Imidazolidinylidene)-5H-dibenzo[a,d]cyclohepten-5-amine compounds are disclosed. The compounds have the property of inhibiting calcium induced contraction of smooth muscle. Certain of the compounds have properties of $\alpha_2$-adrenergic antagonists and others of $\alpha_2$-adrenergic agonists.

12 Claims, No Drawings

N-(2-IMIDAZOLIDINYLIDENE)-5H-DIBENZO[A,D]CYCLOHEPTEN-5-AMINE COMPOUNDS AND α₂-ADRENERGIC ANTAGONISTIC USES THEREOF

DESCRIPTION OF THE INVENTION

The present invention is directed to N-(2-imidazolidinylidene)-5H-dibenzo[a,d]cyclohepten-5-amine compounds which include the guanidine bases represented by Formula I:

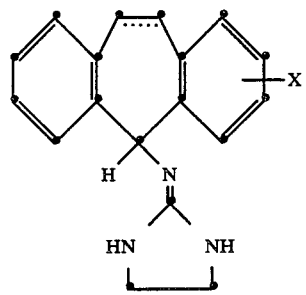

and the acid addition salts thereof. In this and succeeding formulas, the ----- designation between the 10 and 11 positions that the bond may be a saturated single bond or an unsaturated double bond, X may be hydrogen, or halogen such as fluorine bromine, chlorine, or iodine, or lower alkoxy, lower alkylthio, trifluoromethyl, trifluoromethylthio, lower alkyl, cyano, or hydroxy.

A preferred embodiment of the present invention is that in which the linkage between $C_{10}$ and $C_{11}$ is unsaturated so that the group is —CH=CH— and the substituents are in the 3-position as represented by the following formula:

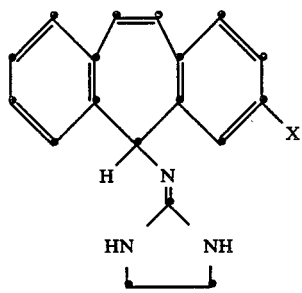

A still more preferred embodiment of the present invention are those in which the X is hydrogen or halogen.

The acid addition salts are those of non-toxic, pharmaceutically acceptable acids and include salts of inorganic acids such as hydrochloric, hydrobromic, hydroiodic, phosphoric, sulfuric, nitric and the like, and organic acids such as acetic, propionic, glycolic, pamoic, pyruvic, malonic, succinic, maleic, fumaric, malic, tartaric, citric, mandelic, benzoic, cinnamic, methanesulfonic, ethanesulfonic, salicyclic, p-toluenesulfonic, cyclohexanesulfamic, and the like and include acids related to the pharmaceutically acceptacle salts listed in Journal of Pharmaceutical Sciences, 66, 2 (1977) and incorporated herein by reference. The hydrohalide salts are especially useful in the preparation of the compounds, permitting a more convenient form for isolation than the free base as hereinafter described.

The compounds of the present invention are inherently capable of existing in tautomeric forms and may be represented by the following tautomeric formulas (Ia)

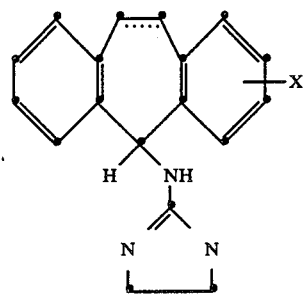

and (Ib)

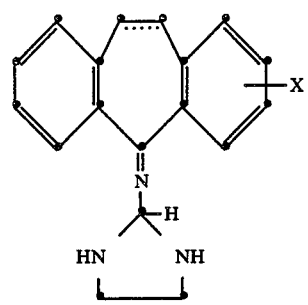

In addition to these tautomeric forms, when X is not hydrogen, i.e., when X is halogen or other substituent, optical isomeric forms of Formula I products are possible. Although the compounds are named as N-(2-imidazolidinylidene) compounds as represented by Formula I, the invention is intended to embrace all tautomeric forms as well as all enantiomeric forms and mixtures thereof.

The products of the present invention which are free bases are solids, soluble in most nonpolar organic solvents. The products which are acid addition salts are crystalline solids having high melting points, being difficultly soluble in most non-polar organic solvents but soluble in aqueous media. The products have several useful pharmacological properties rendering them adaptable for therapeutic applications. Thus, the compounds have shown properties which would render them useful as calcium entry blockers. In addition, the compounds in which X in Formula I is hydrogen show α₂-adrenergic agonist activity while compounds in which X in Formula I is halogen show α₂-adrenergic antagonist activity. The ccmpounds are thus useful in the treatment of cardiovascular diseases as antianginal or antiarrhythmic agents or coronary vasodilators; in addition, those compounds in which X is other than hydrogen, particularly halogen, are further useful in the treatment of depression, hypertension, diabetes, glaucoma, and in inhibiting blood platelet aggregation.

The compounds of the present invention may be obtained by reacting a 5H-dibenzo[a,d]cyclohepten-5-ylamine compound of the formula

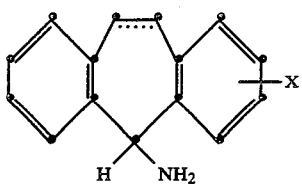

with a 2-methylmercapto-4,5-dihydroimidazole compound of the formula

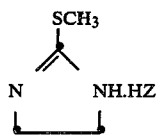

wherein HZ represents a hydrohalide salt. The reaction is carried out in a solvent medium in the presence of an organic base and obtaining the guanidine base of Formula I as the hydrohalide salt. The free base then may be obtained by treating the hydrohalide salt with excess alkali.

The 5H-dibenzo[a,d]cyclohepten-5-ylamine compound starting materials (II) are solids which may be prepared by reducing the appropriate 5H-dibenzo[a,d]cyclohepten-5-one to the corresponding 5-hydroxy compound, then treating the 5-hydroxy compound with thionyl chloride, or hydrogen chloride, or the like to produce the 5-chloro compound which is then caused to react with formamide, followed by basic hydrolysis of the formamide derivative to produce the desired starting material (II) as subsequently described.

The 2-methylmercapto-4,5-dihydroimidazole hydrohalide reactant, also sometimes referred to as 2-methylthio-4,5-dihydroimidazole hydrohalide reactant, is a solid which may be prepared by refluxing ethylenethiourea with a slight excess of methyl halide in absolute ethanol in a manner fully described by Aspinall et al. in *J. Am. Chem. Soc.*, 73, 602-3 (1951).

A solvent is generally employed in carrying out the reaction. Suitable solvents include alcohols such as ethanol, isopropanol, methanol, and other polar solvents such as acetone, methyl ethyl ketone and the like.

A tertiary amine base may be employed to facilitate the reaction. Suitable amines include triethylamine, trimethylamine, pyridine and the like. Secondary and primary amines are not employed in order to avoid competing reactions.

In a preferred procedure, substantially equimolar amounts of the amine reactant of Formula II and imidazole reactant of Formula III as a hydrohalide are employed together with a substantially equimolar amount of tertiary amine. Alternatively, instead of using a tertiary amine, the reaction may be carried out employing two molar portions of the amine compound of Formula II for each molar portion of the imidazole compound of Formula III as the hydrohalide.

In carrying out the reaction, the appropriate 5H-dibenzo[a,d]cyclohepten-5-ylamine compound, the 2-methylmercapto-4,5-dihydroimidazole hydrohalide compound, and the tertiary amine base, if employed, are mixed together in an appropriate solvent and the mixture heated conveniently at reflux temperature, preferably for from about 4 to 24 hours, whereupon a reaction takes place with the formation of the desired N-(2-imidazolidinylidene)-5H-dibenzo[a,d]cyclohepten-5-amine product of Formula I as the hydrohalide in the reaction mixture. The product may be recovered from the reaction mixture by evaporating the solvent, then purifying and crystallizing the residue by conventional procedures.

When the N-(2-imidazolidinylidene)-5H-dibenzo[a,d]cyclohepten-5-amine compound is desired in the form of the free base, the hydrohalide salt is contacted with a large excess of aqueous inorganic base preferably an alkali hydroxide such as sodium hydroxide or potassium hydroxide and the free amine base thus obtained extracted with a water-immiscible organic solvent and then recovered by vaporizing most of the solvent.

The compounds of the present invention possess several pharmacological properties adaptable for therapeutic uses. One of the properties demonstrated by the compounds is inhibition of calcium induced contraction of tracheal smooth muscle or vascular tissue. The property may be observed in a test in which segments of vascular smooth muscle obtained from male Sprague-Dawley rats are suspended in physiological salt solution in a tissue bath instrumented for recording contractions. After the tissue has been equilibrated, washed in calcium-free physiological salt solution and then depolarized, 1.0 mM calcium chloride is re-added to induce contraction. After the contraction has reached a plateau, tissues are washed and a test compound or vehicle is added to determine the effect on a second contraction achieved by the above cyclic protocol. From measuring the initial contraction as well as the second contraction in the presence of the test compound, the extent of inhibition may be calculated.

In this test, N-(2-imidazolidinylidene)-5H-dibenzo[a,d]cyclohepten-5-amine hydroiodide showed 56 percent inhibition at $10^{-7}$ M and N-(2-imidazolidinylidene)-3-bromo-5H-dibenzo[a,d]cyclohepten-5-amine hydroiodide showed 40 percent inhibition at $10^{-7}$M. These results indicate usefulness of the compounds in the study and treatment of cardiovascular diseases. Comparable studies using isolated tracheal smooth muscle (guinea pigs) indicate that these compounds may have utility in spastic disorders of the respiratory tract (e.g. asthma).

The compounds of the present invention also act at α-adrenergic receptor sites exhibiting $\alpha_2$-adrenergic agonist or antagonist activity depending on the nature of the substituent at the 3-position. The α-adrenergic activity may be demonstrated by determining the neurogenic contractions of rat vas deferens. In such determination, vas deferens of rat is suspended under tension between two platinum electrodes of an organ bath containing Tyrode's solution and contractile responses to electrical stimulation recorded. Agonist drug is added and $EC_{50}$ values determined. After wash out, an antagonist drug is added and after a suitable period of contact with the tissue, the $EC_{50}$ values of agonist in presence of antagonist are similarly determined.

In such determinations carried out with the compounds of the present invention, N-(2-imidazolidinylidene)-5H-dibenzo[a,d]cyclohepten-5-amine hydroiodide was found to inhibit neurogenic contractions of the rat vas deferens which was antagonized by rauwolscine. This demonstrates $\alpha_2$-adrenergic agonist activity indicating that the compound would be adaptable for use as an antihypertensive agent.

N-(2-Imidazolidinylidene)-3-bromo-5H-dibenzo[a,d]cyclohepten-5-amine hydroiodide enhanced the neurogenic contractions of the rat vas deferens when given alone but also antagonized the response to methoxamine with a similar order of potency indicating behavior as a partial $\alpha_1$-adrenoreceptor agonist. The compound also antagonized the inhibition of contractions produced by clonidine indicating it is an $\alpha_2$-adrenoreceptor antagonist as well. These properties indicate suitability for use as an antidepressant.

For use in the chemotherapeutic treatment of various diseases, an effective amount of the compounds of the present invention may be administered orally, parenterally, by inhalation, or by suppository, and in any suitable dosage form. For oral administration, the compounds may be offered in the form of tablets or capsules with suitable dispersants and carrier materials or dispersed in a liquid carrier for administration as solution or aqueous dispersion or emulsion; for parenteral administration, the compounds may be dispersed in an appropriate liquid carrier with or without dispersing agents depending on whether a solution, emulsion or other dispersion is intended; for aerosol administration the compound may be dispersed formulated with a suitable dispersant and propellant; and for use as suppository the compounds may be dispersed in a suitable carrier. Suitable carriers and dispersants are hereinafter described.

The ratio of the compound of the present invention to carrier varies with the particular compound, purpose and the mode of administration. The dosage level for the compounds may be varied from about 0.05 milligram to about 7.0 milligrams per kilogram of body weight per day. Daily doses in the range of 1 to 3.5 mg/kg are preferred. These doses are suitable for any of the utilities described herein.

The compounds may be administered in pharmaceutically acceptable acid addition salt form. Such acid addition salt forms exhibit the same order of activity as the free base forms and may be obtained during a preferred synthetic procedure in the case of hydrohalides or may be prepared from the free base according to conventional procedures.

The free base or salt may be formulated with a pharmaceutical carrier or diluent.

To prepare the pharmaceutical compositions of this invention, guanidine base compound of Formula (I) or acid addition salt thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients may be included, for purposes such as, for example, for aiding solubility or for preservation. Injectable suspensions also may be prepared, in which case appropriate liquid carriers, suspending agents and the like may be employed. The pharmaceutical compositions herein will contain, per dosage unit, e.g., tablet, capsule, powder, injection, teaspoonful and the like, from about 10 to about 500 mg. of the active ingredient, preferably, from about 10 to about 250 mg.

The following examples illustrate the invention but are not to be construed as limiting:

EXAMPLE I

N-(2-Imidazolidinylidene)-3-bromo-5H-dibenzo[a,d]cyclohepten-5-amine Hydroiodide

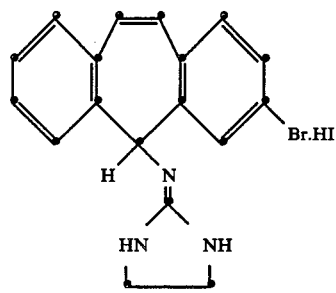

6.90 grams (0.024 mole) of 3-bromo-5H-dibenzo[a,d]cycloheptene-5-ylamine, 2.95 grams (0.012 mole) of 2-methylmercapto-4,5-dihydroimidazole hydroiodide, and 65 milliliters of absolute ethanol were stirred together and refluxed for 28 hours. At the end of this period, the solvent was evaporated under reduced pressure and the residue triturated with five 100 milliliter portions of diethyl ether to obtain a purified residue. The purified residue was dissolved in 20 milliliters of absolute ethanol and 300 milliliters of ether added thereto whereupon a solid precipitated. The mixture was stirred thoroughly, the solvent decanted to obtain a residue which was placed on a Still-silica column and eluted with 5 percent methanol in chloroform. The eluted fractions were examined by thin layer chromatography (TLC), the homogeneous TLC fractions combined, and the solvent then vaporized to obtain the desired N-(2-imidazolidinylidene)-3-bromo-5H-dibenzo[a,d]cyclohepten-5-amine hydroiodide product as residue. The product was crystallized from chloroform to obtain purified product, m.p. 240°–241° C. (dec.). Elemental analyses were as follows: Calc'd for $C_{18}H_{17}BrIN_3$: C, 44.84; H, 3.55; N, 8.72. Found: C, 44.75; H, 3.48; N, 8.46.

EXAMPLE II

N-(2-Imidazolidinylidene)-5H-dibenzo[a,d]cyclohepten-5-amine Hydroiodide 1.04 grams (0.005 mole) of 5H-dibenzo[a,d]cyclohepten-5-ylamine, 1.22 grams (0.005 mole) of 2-methylmercapto-4,5-dihydroimidazole hydroiodide, and 1.5 milliliters of triethylamine were mixed together in 20 milliliters of ethanol and heated at reflux temperature for 16 hours. Thereafter most of the ethanol was evaporated, some n-butanol added and the resulting mixture heated under reflux for 15 hours. At the end of this period, the solvent was removed under reduced pressure, and residue obtained to which was added first, aqueous sodium bicarbonate, then ether and the resulting mixture stirred and decanted to recover the non-dissolving solid as residue. The solid was stirred overnight with ether, filtered and crystallized from ethanol. It was purified by chromatographing on a silica gel column employing 6 percent methanol in chloroform as eluant to obtain the desired N-(2-imidazolidinylidene)-5H-dibenzo[a,d]cyclohepten-5-amine hydroiodide product. Elemental analyses were as follows:

Calc'd for $C_{18}H_{18}IN_3$: C, 53.61; H, 4.49; N, 10.42. Found: C, 54.25; H, 4.63; N, 10.63.

EXAMPLE III

In an operation carried out in a manner similar to that described in Example II, N-(2-imidazolidinylidene)-5H-dibenzo[a,d]cyclohepten-5-amine hydroiodide was obtained by the reaction of 4.14 grams (0.02 mole) of 5H-dibenzo-[a,d]cyclohepten-5-ylamine, 2.44 grams (0.01 mole) of 2-methylmercapto4,5-dihydroimidazole hydroiodide in 50 milliliters of ethanol, which after purification by crystallizing from ethanol, chromatographing through a Still column and drying under reduced pressure had a melting point of 210°–212° C. Elemental analyses were as follows:

Calc'd for $C_{18}H_{18}IN_3$: C, 53.61; H, 4.49; N, 10.42. Found: C, 53.65; H, 4.62; N, 10.51.

EXAMPLE IV

In an operation carried out in a manner similar to that described in Example I, the following compounds may be prepared:

, N-(2-Imidazolidinylidene)-3-chloro-5H-dibenzo[a,d]cyclohepten-5-amine hydrochloride from 3-chloro-5H-dibenzo[a,d]cycloheptene-5-ylamine and 2-methylmercapto-4,5-dihydroimidazole hydrochloride.

N-(2-Imidazolidinylidene)-3-iodo-5H-dibenzo[a,d]cyclohepten-5-amine hydroiodide from 3-iodo-5H-dibenzo[a,d]cycloheptene-5-ylamine and 2-methylmercapto-4,5-dihydroimidazole hydroiodide.

EXAMPLE V

The following free bases may be prepared by mixing together the hydrohalides of the imidazolidinylidene-2-amines as described in the foregoing examples with dilute base, extracting the amine with toluene, thereafter evaporating the solvent. The amines then may be purified by crystallization.

N-(2-Imidazolidinylidene)-3-bromo-5H-dibenzo[a,d]cyclohepten-5-amine.

N-(2-Imidazolidinylidene-5H-dibenzo[a,d]cyclohepten-5-amine.

N-(2-Imidazolidinylidene)-3-chloro-5H-dibenzo[a,d]cyclohepten-5-amine.

N-(2-Imidazolidinylidene)-3-iodo-5H-dibenzo[a,d]cyclohepten-5-amine.

EXAMPLE VI

The following salts may be prepared by intimately mixing the free guanidine base prepared as above described with an ethanolic solution of the acid and recovering the salt.

N-(2-Imidazolidinylidene)-3-bromo-5H-dibenzo[a,d]cyclohepten-5-amine hydrogen phosphate.

N-(2-Imidazolidinylidene)-5H-dibenzo[a,d]cyclohepten-5-amine hydrogen maleate.

N-(2-Imidazolidinylidene)-5H-dibenzo[a,d]cyclohepten-5-amine hydrochloride.

EXAMPLE VII

In operations carried out in a manner similar to that described in Example I, the following compounds may be prepared:

N-(2-Imidazolidinylidene)-3-methoxy-5H-dibenzo[a,d]cyclohepten-5-amine hydroiodide from 3-methoxy-5H-dibenzo[a,d]-cyclohepten-5-ylamine and 2-methylmercapto-4,5-dihydroimidazole hydroiodide.

N-(2-Imidazolidinylidene)-2-methyl-5H-dibenzo[a,d]cyclohepten-5-amine hydroiodide from 2-methyl-5H-dibenzo[a,d]-cyclohepten-5-ylamine and 2-methylmercapto-4,5-dihydroimidazole hydroiodide.

N-(2-Imidazolidinylidene)-1-ethyl-5H-dibenzo [a,d]cyclohepten-5-amine hydroiodide from 1-ethyl-5H-dibenzo[a,d]cyclohepten-5-ylamine and 2-methylmercapto-4,5-dihydroimidazole hydroiodide.

N-(2-Imidazolidinylidene)-3-trifluoromethylthio-5H-dibenzo[a,d]cyclohepten-5-amine hydrobromide from 3-trifluoromethylthio-5H-dibenzo[a,d]-cyclohepten-5-ylamine and 2-methylmercapto-4,5-dihydroimidazole hydrobromide.

N-(2-Imidazolidinylidene)-2-methylmercapto-5H-dibenzo[a,d]cyclohepten-5-amine hydrochloride from 2-methylmercapto-5H-dibenzo[a,d]-cyclohepten-5-ylamine and 2-methylmercapto-4,5-dihydroimidazole hydrochloride.

N-(2-Imidazolidinylidene)-3-cyano-5H-dibenzo [a,d]cyclohepten-5-amine hydrobromide from 3-cyano-5H-dibenzo[a,d]cyclohepten-5-ylamine and 2-methylmercapto-4,5-dihydroimidazole hydrobromide.

N-(2-Imidazolidinylidene)-3-hydroxy-5H-dibenzo [a,d]cyclohepten-5-amine hydrochloride from 3-hydroxy-5H-dibenzo[a,d]-cyclohepten-5-ylamine and 2-methylmercapto-4,5-dihydroimidazole hydrochloride.

N-(2-Imidazolidinylidene)-4-fluoro-5H-dibenzo [a,d]cyclohepten-5-amine hydrobromide from 4-fluoro-5H-dibenzo-[a,d]cyclohepten-5-ylamine and 2-methylmercapto-4,5-dihydroimidazole hydrobromide.

EXAMPLE VIII

In still further operations carried out in a manner similar to that described in Example I, the following compounds may be prepared:

N-(2-Imidazolidinylidene)-3-bromo-10,11-dihydro-5H-dibenzo[a,d]cyclohepten-5-amine hydrobromide from 3-bromo-10,11-dihydro-5H-dibenzo [a,d]cyclohepten-5-ylamine and 2-methylmercapto-4,5-dihydroimidazole hydrobromide.

N-(2-Imidazolidinylidene)-10,11-dihydro-5H-dibenzo[a,d]cyclohepten-5-amine hydroiodide from 10,11-dihydro-5H-dibenzo[a,d]cyclohepten-5-ylamine and 2-methylmercapto-4,5-dihydroimidazole hydroiodide.

N-(2-Imidazolidinylidene)-3-iodo-10,11-dihydro-5H-dibenzo[a,d]cyclohepten-5-amine hydroiodide from 3-iodo-10,11-dihydro-5H-dibenzo[a,d]cyclohepten 5-ylamine and 2-methylmercapto-4,5-dihydroimidazole hydroiodide.

N-(2-Imidazolidinylidene)-3-trifluoromethyl-10,11-dihydro-5H-dibenzo[a,d]-cyclohepten-5-amine hydroiodide from 3-trifluoromethyl-10,11-dihydro-5H-dibenzo[a,d]cyclohepten-5-ylamine and 2-methylmercapto-4,5-dihydroimidazole hydroiodide.

N-(2-Imidazolidinylidene)-2-methoxy-10,11-dihydro-5H-dibenzo[a,d]cyclohepten-5-amine hydroiodide from 2-methoxy-10,11-dihydro-5H-dibenzo [a,d]cyclohepten-5-ylamine and 2-methylmercapto-4,5-dihydroimidazole hydroiodide.

N-(2-Imidazolidinylidene)-2-methylmercapto-10,11-dihydro-5H-dibenzo[a,d]cyclohepten-5-amine hydroiodide from 2-methylmercapto-10,11-dihydro-5H-dibenzo[a,d]cyclohepten-5-ylamine and 2-methylmercapto-4,5-dihydroimidazole hydroiodide.

N-(2-Imidazolidinylidene)-2-isopropyl-10,11-dihydro-5H-dibenzo[a,d]cyclohepten-5-amine hydroiodide from 2-isopropyl-10,11-dihydro-5H-dibenzo [a,d]cyclohepten-5-ylamine and 2-methylmercapto-4,5-dihydroimidazole hydroiodide.

N-(2-Imidazolidinylidene)-2-hydroxy-10,11-dihydro-5H-dibenzo[a,d]cyclohepten-5-amine hydroiodide from 2-hydroxy-10,11-dihydro-5H-dibenzo[a,d]cyclohepten-5-ylamine and 2-methylmercapto-4,5-dihydroimidazole hydroiodide.

N-(2-Imidazolidinylidene)-3-cyano-10,11-dihydro-5H-dibenzo[a,d]cyclohepten-5-amine hydroiodide from 3-cyano-10,11-dihydro-5H-dibenzo[a,d]cyclohepten-5-ylamine and 2-methylmercapto-4,5-dihydroimidazole hydroiodide.

EXAMPLE IX

Tablets are prepared from a tablet composition comprising:

| | |
|---|---|
| N—(2-Imidazolidinylidene)-3-bromo-5H—dibenzo[a,d]cyclohepten-5-amine | 0.2 part by weight |
| Magnesium stearate | 1 |
| Polyvinylpyrrolidine | 4 |
| Talc | 5 |
| Starch | 10 |
| Lactose | 137.8 |
| Dimethylsilicone oil | 0.5 |
| Polyethylene glycol 6000 | 1.5 | by intimately blending the dry ingredients, thereafter adding the liquid ingredients and feeding into a tablet press to obtain the desired tablets containing 0.2 milligram of the active ingredient.

EXAMPLE X

Capsules for oral use each containing 1 milligram of N-(2-imidazolidinylidene)-5H-dibenzo[a,d]cyclohepten-5-amine are prepared by blending 1 gram of said amine compound with 287 grams of lactose and 4.1 grams of magnesium stearate. This is then used to fill 1000 capsules each containing 1 milligram of N-(2-imidazolidinylidene)-5H-dibenzo[a,d]cyclohepten-5-amine.

EXAMPLE XI

An injectable solution employing N-(2-imidazolidinylidene)-3-bromo-5H-dibenzo[a,d]cyclohepten5-amine is prepared by mixing together 1 gram of said amine compound, 9 grams of sodium chloride and distilled water to 1 liter. One milliliter portions of said injectable solution may be employed to administer 1 milligram of N-(2-imidazolidinylidene)-3-bromo-5H-dibenzo[a,d]cyclohepten-5-amine.

EXAMPLE XII

A liquid suspension may be prepared by mixing together 5.0 grams ot N-(2-imidazolidinylidene)-5H-dibenzo[a,d]cyclohepten-5-amine hydrochloride, 3.0 grams of Veegand H.V., 1.0 gram of methyl paraben, 10.0 grams of kaolin, 250 grams of glycerine and water to 1 liter. The suspension may be administered in an amount suitable for supplying the desired dose of N-(2-imidazolidinylidene)-5H-dibenzo[a,d]cyclohepten-5-amine active ingredient.

The 5H-dibenzo[a,d]cyclohepten-5-ylamine starting material of Formula II may be prepared from an appropriate 5H-dibenzo-[a,d]cyclohepten-5-one represented by the formula:

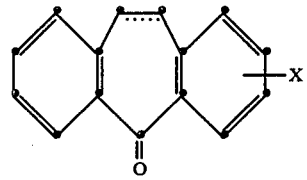

which may be prepared by a method described by A. C. Cope et al., J. Am. Chem. Soc., 73, 1673–8 (1951). The substituent X may already be in place when the ketone is formed by using appropriate starting materials in the Cope procedure. With certain substituents, the desired X may be achieved by replacing the halogen in the corresponding haloketone, preferably bromoketone or iodoketone. Thus, when X is —SCF$_3$ or —S-lower alkyl, the appropriate ketone may be prepared by reacting a corresponding haloketone with a molar excess of bis(trifluoromethylthio)-mercury or bis-(lower alkylthio)-mercury and large excess of copper dust in a solvent such as dimethylformamide or a tertiary amine and heated at about 100°–200° C. for time sufficient to complete the reaction with the formation of a trifluoromethylthio-5H-dibenzo [a,d]cyclohepten-5-one or loweralkylthio-5H-dibenzo[a,d]cyclohepten-5-one. Similarly, when X is CN, the ketone reactant may be prepared by reacting the appropriate corresponding haloketone with a two-fold molar excess of cuprous cyanide in an inert solvent such as dimethylformamide and heating for time sufficient to complete the reaction with the formation of a cyano-5H-dibenzo[a,d]-cyclohepten-5-one. The lower alkoxy group may also be introduced by replacing a halogen by reacting excess sodium alkoxide in an inert solvent such as dimethylformamide. Ketones in which X is hydroxide are conveniently prepared by effecting cleavage of the alkoxy group by heating, for example, in pyridine hydrochloride at about 200° C. Procedures described by T. W. Campbell et al. in Helv. Chem. Acta 36, 1489–1499 (1953) also may be adapted for the preparation of the starting ketones.

In the preparation of the amine starting material from the ketone, the ketone is first reduced to the corresponding alcohol, conveniently by adding dropwise an aqueous solution containing molar excess (about 2.5 molar excess) of sodium borohydride to a boiling alcohol solution of the ketone and thereafter heating at reflux temperature until completion of the reaction with the formation of the corresponding hydroxy compound which is recovered employing conventional procedures. The hydroxy compound then is refluxed with molar excess thionyl chloride to obtain the corresponding chloro compound in the reaction mixture; the chloro compound is recovered as residue after adding benzene to the reaction mixture and codistilling the excess thionyl chloride. The chloro compound then is dissolved in an excess of formamide and the solution is stirred and heated at 80° C. for 1 hour. The solid is removed by filtration, washed with water, collected, and dried. The formamide compound is hydrolyzed by refluxing with sodium hydroxide in an aqueous ethanolic solution for 2 to 4 hours. The desired amine compound of Formula II may be recovered by conventional procedures such as pouring the reaction mixture into water, extracting with inert water-immiscible solvent, drying, and recovering the amine by evaporating the solvent.

What is claimed is:

1. A compound having the structure:

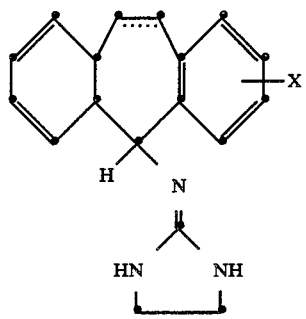

wherein ----- the designation between the 10 and 11 positions indicates that the bond may be a saturated single bond or an unsaturated double bond, X is hydrogen, halogen, lower alkoxy, lower alkylthio, trifluoromethyl, trifluoromethylthio, lower alkyl cyano or hydroxy; and pharmaceutically acceptable salts thereof.

2. A compound according to claim 1 in which the group at the 10 and 11 positions is unsaturated, —CH=CH—.

3. A compound according to claim 1 in which X is hydrogen.

4. A compound according to claim 1 in which X is halogen.

5. A compound according to claim 1 in which X is at the 3-position.

6. N-(2-Imidazolidinylidene)-3-bromo-5H-dibenzo[a,d]cyclohepten-5-amine.

7. A compound according to claim 6 as a hydroiodide salt.

8. N-(2-Imidazolidinylidene)-5H-dibenzo[a,d]cyclohepten-5-amine.

9. A compound according to claim 8 as a hydroiodide salt.

10. A pharmaceutical composition useful for treating (a) cardiovascular diseases, (b) spastic disorders of the respiratory tract, (c) hypertension, or (d) depression comprising a therapeutically effective amount of a compound having the structure:

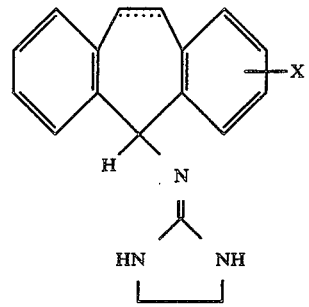

wherein the ----- bond designation between the 10 and 11 positions indicates that the bond may be a saturated single bond or an unsaturated double bond, X is hydrogen, halogen, lower alkoxy, lower alkylthio, trifluoromethyl, trifluoromethylthio, loweralkyl, cyano, or hydroxy; and pharmaceutically acceptable salts thereof, said compound being in intimate admixture with a pharmaceutically acceptable carrier.

11. A method of treating hypertension which comprises administering an effective antihypertensive amount of a compound having the structure:

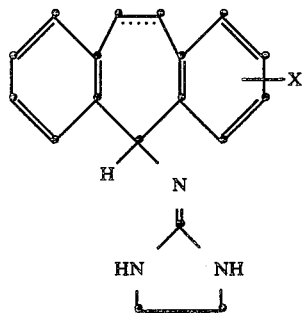

wherein the ----- bond designation between the 10 and 11 positions indicates that the bond may be a saturated signle bond or an unsaturated double bond, X is hydrogen, halogen, lower alkoxy, lower alkylthio, trifluoromethyl, trifluoromethylthio, loweralkyl, cyano, or hydroxy; and pharmaceutically acceptable salts thereof.

12. A method of treating depression which comprises administering an effective antidepressant amount of a compound having the structure:

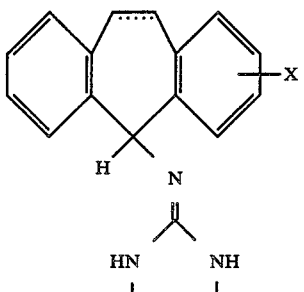

wherein the ----- bond designation between 10 11 positions indicates that the bond may be a saturated single bond or an unsaturated double bond, X is halogen, lower alkoxy, lower alkylthio, trifluoromethyl, trifluoromethylthio, lower alkyl, cyano or hydroxy, and pharmaceutically acceptable salts thereof.

* * * * *

UNITED STATES PATENT AND TRADEMARK OFFICE
CERTIFICATE OF CORRECTION

PATENT NO. : 4,590,202
DATED : May 20, 1986
INVENTOR(S) : David C. Remy

It is certified that error appears in the above—identified patent and that said Letters Patent is hereby corrected as shown below:

Col. 11, line 33, after wherein insert -- the --, and after ----- "the" should read --bond--

Col. 12, line 62, after 10 insert -- and --

Col. 11, line 33; Claim 10, column 12, line 15;

Col. 12, line 40 and col. 12, line 62, change "-----" to -- ⎯⎯ --

Signed and Sealed this

Seventh Day of October, 1986

[SEAL]

*Attest:*

DONALD J. QUIGG

*Attesting Officer*      *Commissioner of Patents and Trademarks*